Re. 16,593

Reissued Apr. 19, 1927.

UNITED STATES PATENT OFFICE.

JOHANNES FRENG AND EINAR BERGVE, OF OSLO, NORWAY.

METHOD FOR PRODUCING A DISINFECTING OR CLEANSING SPRAY FOR HYGIENIC AND MEDICAL PURPOSES.

No Drawing. Original No. 1,522,610, dated January 13, 1925, Serial No. 379,597, filed May 7, 1920. Application for reissue filed January 6, 1927. Serial No. 159,496.

This invention has for its object the method of producing a liquid dentifrice. A characteristic feature of the invention is the impregnation of an aqueous solution that forms the base of the dentifrice with carbonic acid. The pressure should be at least three atmospheres.

It is known to effect the cleansing or disinfection of the teeth and of the mouth by means of atomizers. Such atomizers have attained an extended use by dentists and physicians. In these known atomizers a liquid disinfectant is atomized by means of air under a pressure of about 5 atmospheres.

According to the present invention an improved effect of the liquid dentifrice is obtained by impregnating the cleansing or disinfecting liquid with carbonic acid immediately before it is applied. This impregnation is suitably brought about by atomizing the liquid by means of carbonic acid gas or gas rich in carbonic acid instead of using air for this purpose. To increase the carbonic acid content of the atomized liquid it may also be suitable to pass a current of gaseous carbonic acid under pressure through the liquid previously to its being atomized by the carbonic acid gas. The atomizing as well as the impregnation may be effected by means of pure carbonic acid or by means of a gas rich in carbonic acid; for instance, a mixture of carbonic acid and air containing 30 per cent of $CO_2$ has been found to be very suitable. Instead of using a mixture of carbonic acid and air it may be suitable in some instances to employ pure nitrogen or pure oxygen as an admixture.

It has been found that a spray produced in the manner above described and being rich in carbonic acid when used to clean the teeth and the mouth has a very refreshing influence and stimulates the gums. It has also been found that this carbonic acid spray has an emulsifying action upon the saliva so that an increased efficiency is attained in regard to the disinfection as well as in regard to the mechanical cleansing.

The carbonic acid may be obtained from any suitable source and the required pressure may be created therein by different means. Thus the carbonic acid may be produced by the action of an acid upon carbonate of lime or other carbonate.

Commercial liquid carbonic acid in steel flasks may also be employed. In this case it will be of advantage to fill the liquid carbonic acid into small flasks of such a size as to allow of being easily carried by the hand. The flask may, for example contain about 2 to 5 kilogrammes. These flasks may then be connected with the atomizer through pipes provided with pressure controlling means. As long as liquid carbonic acid is contained in the flask a constant pressure is maintained, viz., at ordinary temperature about 40–50 atmospheres. By the strong evaporation which takes place when the valve is opened solid carbonic acid may be produced which may obstruct the capillary boring of the atomizer nozzle. This difficulty may be avoided by the insertion of an electric heat element. The atomizer nozzle employed may be constructed according to known principles.

The cleansing or disinfecting liquid becomes atomized in the nozzle by the action of the compressed gas current and is mixed with air until the desired velocity is attained. In a usual dentifrice atomizer about 1 liter of carbonic acid gas (of atmospheric pressure) will be consumed to wash the teeth one time. When the concentration of carbonic acid dissolved in the sprayed liquid is sufficiently high the spray besides having a disinfecting and cleansing effect will also act to promote the solution of the calcareous deposits on the teeth. As is known this deposit consists of about 70 per cent of tricalcium phosphate, about 8 per cent of calcium carbonate and the rest of organic substances. Thus to dissolve this deposit the dentifrice must show a sufficient acidity but at the same time the dentifrice must not act too strongly upon the mucous membranes of the mouth.

The applicants have now found that these requirements are fulfilled by the carbonic acid. It has been found however that to attain a sufficiently strong dissolving action the liquid to be atomized should be impregnated with carbonic acid under pressure before it is atomized so that a solution saturated with carbonic acid at a superatmospherical pressure is produced. This may be attained by placing the pipe, through which compressed carbonic acid is conveyed to the atomizer by means of two channels, in communication with the bottom and top portions of a bottle containing the liquid to be atomized so as to cause the carbonic acid gas to bubble through the liquid. To avoid a too rapid escape of carbonic acid when the pressure is relieved the viscosity of the liquid may be increased by suitable additions such as for example glycerin.

When liquid containing perborates is treated with carbonic acid under pressure as above described the carbonic acid will react upon the perborate so as to produce hydrogen peroxide or oxygen respectively, which thus comes to action in status nascenti.

We claim—

1. Method for the production of a cleaning and disinfecting spray which consists in atomizing a liquid dentifrice containing a perborate by means of a high pressure carbonic acid gas.

2. Method for the production of a cleansing and disinfecting spray which consists in impregnating a liquid dentifrice containing a perborate with carbonic acid gas, and thereupon atomizing the impregnated liquid by means of a high pressure carbonic acid gas.

3. Method for the production of a dental spray, which comprises spraying a liquid dentifrice capable of splitting off oxygen, by means of carbon di-oxide and also dissolved in the dentifrice to cause the solution of tartar and the liberation of oxygen as an antiseptic.

4. Method of cleansing teeth, which comprises spraying a liquid dentifrice saturated with carbon dioxide onto the teeth, whereby the carbon dioxide released at the teeth will produce an emulsion of the saliva and simultaneously dissolve tartar.

5. Method of cleansing teeth, which comprises spraying a liquid dentifrice saturated with gas composed of a mixture of carbon dioxide and another gas inert to carbonic acid, onto the teeth, whereby the carbon dioxide released at the teeth will produce an emulsion of the saliva and permit the carbon dioxide to dissolve tartar.

6. Method of cleansing teeth, which comprises spraying a liquid dentifrice capable of splitting off oxygen, and having carbon dioxide gas also dissolved in said dentifrice, onto the teeth whereby an emulsion is made of the saliva, permitting the dioxide to dissolve the tartar and liberate oxygen as an antiseptic.

7. Method of cleansing teeth, which comprises applying nascent hydrogen peroxide and nascent oxygen at the place being treated by spraying a liquid dentifrice containing carbon dioxide under pressure onto the teeth.

In testimony that we claim the foregoing as our invention, we have hereunto signed our names.

JOHANNES FRENG.
EINAR BERGVE.